United States Patent
Wong et al.

(10) Patent No.: US 9,534,235 B2
(45) Date of Patent: Jan. 3, 2017

(54) EFFICIENT STERILIZATION OF FISH BY DISRUPTION OF GERM CELL DEVELOPMENT

(75) Inventors: Ten-Tsao Wong, West Lafayette, IN (US); Paul Collodi, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 13/982,418

(22) PCT Filed: Dec. 2, 2011

(86) PCT No.: PCT/US2011/063126
§ 371 (c)(1),
(2), (4) Date: Jul. 29, 2013

(87) PCT Pub. No.: WO2012/106026
PCT Pub. Date: Aug. 9, 2012

(65) Prior Publication Data
US 2013/0312127 A1    Nov. 21, 2013

Related U.S. Application Data

(60) Provisional application No. 61/438,312, filed on Feb. 1, 2011.

(51) Int. Cl.
| | |
|---|---|
| *A01K 67/00* | (2006.01) |
| *A01K 67/033* | (2006.01) |
| *C12N 15/85* | (2006.01) |
| *A01K 67/027* | (2006.01) |
| *C07K 14/52* | (2006.01) |
| *C07K 14/54* | (2006.01) |

(52) U.S. Cl.
CPC ....... *C12N 15/8509* (2013.01); *A01K 67/0275* (2013.01); *C07K 14/522* (2013.01); *C07K 14/5415* (2013.01); *A01K 2217/052* (2013.01); *A01K 2217/203* (2013.01); *A01K 2217/206* (2013.01); *A01K 2227/40* (2013.01); *A01K 2267/02* (2013.01); *A01K 2267/0393* (2013.01)

(58) Field of Classification Search
CPC ............. A01K 2227/40; A01K 2217/058; A01K 2217/052
See application file for complete search history.

(56) References Cited

U.S. PATENT DOCUMENTS

| | | |
|---|---|---|
| 7,194,978 B2 | 3/2007 | Zohar et al. |
| 7,834,239 B2 | 11/2010 | Gong et al. |

OTHER PUBLICATIONS

Huang, 2005, Developmental Dynmaics, 233:1294-1303.*
Sun, Acta Biochim Biophys Sin, 2007, 39:235-246.*
Shoji (2008, Developmental Growth Differ . . . . 50:401-406).*
Ali, P., et al., "Growth Improvement in Carp, *Cyprinus carpio* (Linnaeus), Sterilized with 17alpha-Methyltestosterone", "Aquaculture", 1989, pp. 157-167, vol. 76.
Arai, K., "Genetic improvement of aquaculture finfish species by chromosome manipulation techniques in Japan", "Aquaculture", Jun. 1, 2001, pp. 205-228, vol. 197, No. 1-4.
Department of Ecology, State of Washington, "Aquatic Plant Management—Triploid Grass Carp", "http://www.ecy.wa.gov/programs/wq/plants/management/aqua024.html (Accessed Apr. 9, 2014)", May 2001, pp. 1-4.
Donaldson, E., et al., "Current Status of Induced Sex Manipulation", "Proceedings of the Third Annual International Symposium of the Reproductive Physiology of Fish", Aug. 1987, pp. 108-119, Published in: St. John's, Newfoundland, Canada.
Food and Agriculture Organization of the United Nations, "Fishery and Aquaculture Statistics", "FAO Yearbook", 2007, pp. 1-101.
Fueshko, S., et al., "GABA Inhibits Migration of Luteinizing Hormone-Releasing Hormone Neurons in Embryonic Olfactory Explants", "The Journal of Neuroscience", Apr. 1, 1998, pp. 2560-2569, vol. 18, No. 7.
Hu, W., et al., "Antisense for gonadotropin-releasing hormone reduces gonadotropin synthesis and gonadal development in transgenic common carp (*Cyprinus carpio*)", "Aquaculture", 2007, pp. 498-506, vol. 271.
Johnstone, R., "Section I.2.D: Maturity control in Atlantic salmon", "Recent Advances in Aquaculture (Muir, J., et al., Eds.)", 1993, pp. 99-105, Published in: London.
Molyneaux, K., et al., "The chemokine SDF1/CXCL12 and its receptor CXCR4 regulate mouse germ cell migration and survival", "Development", 2003, pp. 4279-4286, vol. 130.
Rottmann, R., et al., "Induction and Verification of Triploidy in Fish", "Southern Regional Aquaculture Center Publication No. 427", Nov. 1991, pp. 1-2.
Slanchev, K., et al., "Development without germ cells: The role of the germ line in zebrafish sex differentiation", "PNAS", Mar. 15, 2005, pp. 4074-4079, vol. 102, No. 11.
Uzbekova, S., et al., "Transgenic rainbow trout expressed sGnRH-antisense RNA under the control of sGnRH promoter of Atlantic salmon", "Journal of Molecular Endocrinology", 2000, pp. 337-350, vol. 25.
Blaser, H., et al., "Migration of Zebrafish Primordial Germ Cells: A Role for Myosin Contraction and Cytoplasmic Flow", "Developmental Cell", Nov. 2006, pp. 613-627, vol. 11.
Doitsidou, M., et al., "Guidance of Primordial Germ Cell Migration by the Chemokine SDF-1", "Cell", Nov. 27, 2002, pp. 647-659, vol. 111.

(Continued)

*Primary Examiner* — Valarie Bertoglio
(74) *Attorney, Agent, or Firm* — Hultquist, PLLC; Steven J. Hultquist (57) ABSTRACT

Methods of disrupting germ cell migration and development in a fish embryo by inducing targeted expression of Sdf-1a or Lif and disruption of the Sdf-1a gradient or a Lif signaling pathway in the fish embryo have been developed. Plasmid constructs containing a gene encoding Sdf-1a or Lif and a gene encoding a signaling sequence for targeted expression of Sdf-1a or Lif have been generated. The plasmids will be administered to a fish or a population of fish to reproductively sterilize the population with efficacy of up to 100%. Transgenic fish of this invention are reproductively incompetent of genetically contaminating a wild fish population.

8 Claims, 9 Drawing Sheets

(56) References Cited

OTHER PUBLICATIONS

Dumstrei, K., et al., "Signaling pathways controlling primordial germ cell migration in zebrafish", "Journal of Cell Science", 2004, pp. 4787-4795, vol. 117.
Fan, L., et al., "Zebrafish Primordial Germ Cell Cultures Derived from vasa::RFP Transgenic Embryos", "Stem Cells and Development", 2008, pp. 585-597, vol. 17.
Wong, T., et al., "Effects of specific and prolonged expression of zebrafish growth factors, Fgf2 and Lif in primordial germ cells in vivo", "Biochem Biophys Res Commun", Nov. 21, 2012, pp. 347-351, vol. 430.

\* cited by examiner

FIG. 1A
Sdf-1a gradient guides migration

FIG. 1B

FIG. 1C
Mis-migration of PGCs

A. Inducible Sdf-1a or Lif expression in embryos using *Tet-on*, *mt-II* or *hsp* promoters B. Inducible Sdf-1a or Lif expression in double transgenic embryos of a Tet-off system
*Tg(TRE-tight:sdfia-nanos)/Tg(nanos:Tet-off adv-nanos)*
*Tg(TRE-tight:sdfia-nanos)/Tg(kop:Tet-off adv-nanos)*
*Tg(TRE-tight:lif-nanos)/Tg(nanos:Tet-off adv-nanos)*
*Tg(TRE-tight:lif-nanos)/Tg(kop:Tet-off adv-nanos)*

FIG. 4

**A. Inducible Sdf-1a or Lif expression in embryos by treating brood stock using *Tet-on*, *mt-II* or *hsp* promoters.**

B. Inducible Sdf-1a or Lif expression in embryos of a Tet-off system

EFFICIENT STERILIZATION OF FISH BY DISRUPTION OF GERM CELL DEVELOPMENT

CROSS-REFERENCE TO RELATED APPLICATIONS

This application is a U.S. national phase under the provisions of 35 U.S.C. §371 of International Patent Application No. PCT/US11/63126 filed Dec. 2, 2011, which in turn claims priority of U.S. Provisional Application No. 61/438,312, filed Feb. 1, 2011. The disclosures of such international patent application and U.S. priority provisional application are hereby incorporated herein by reference in their respective entireties, for all purposes.

FIELD OF THE INVENTION

The present invention relates to methods for the production of reproductively sterile populations of fish for aquaculture and aquariums and control of invasive fish species. The methods include disruption of the Sdf-1a signaling pathway or a Lif signaling pathway, leading to the failure of normal PGC migration. The present invention also relates to fish generated by methods of the invention and to plasmid constructs used in the methods of the invention.

DESCRIPTION OF THE RELATED ART

According to data from the United Nations Food and Agriculture Organization (FAO), world seafood consumption has doubled every 20 to 25 years since 1950 [FAO. 2007 Fishery and Aquaculture Statistics. Rome: Food and Agriculture Organization of the United Nations, 2007.]. Today most traditional fisheries are being harvested at maximum yields while populations of almost all commercial marine fisheries species around the world are undergoing a dramatic decrease due to over-fishing. In the United States seafood consumption has increased 60% since 1960 and approximately 85% of this demand each year is met by imported fish and shellfish resulting in approximately $7 billion annual trade deficit in edible fishery products [NOAA. Fish Watch U.S. Seafood Fact. In; 2010. Hyper text transfer protocol world wide web address nmfs.noaa.gov/fishwatch/trade_and_aquaculture.htm].

Aquaculture, also known as "fish farming," is becoming increasingly important to offset this deficiency in aquatic foods production, and dramatic increases in aquaculture production have been made over the last few decades. From 2002 to 2007 annual aquaculture production increased from 36.8 million tons to 50.3 million tons with a total value of $87 billion [FAO. 2007 Fishery and Aquaculture Statistics. Rome: Food and Agriculture Organization of the United Nations, 2007.]. As this shift in dependence from wild populations to artificially propagated aquatic species continues, optimization of aquaculture methods will be necessary to maximize food production. Increased reliance on aquaculture production throughout the world will also require that environmentally sustainable commercial fish farming methods are implemented that have minimal ecological impact.

One concern regarding the ecological impact is the disturbance by the aquaculture system of natural ecosystems. Such disturbances can threaten local wild species. In particular, escaped farmed species can swell the total number of fish in an area, causing overcrowding of a natural habitat and competing with the wild fish for resources. The escaped farmed species can interfere with the life cycles of the wild species, eventually displacing the wild species and, potentially, driving the local population to extinction. As the fish population reproduces, the problems increase exponentially. Responsible and sustainable aquaculture systems will address these problems.

One approach to optimizing aquaculture production in an environmentally sustainable way is by farming reproductively sterile populations of fish. Sterilization of commercially farmed fish increases their growth rate by enhancing the conversion of food energy to muscle growth instead of gonadal development and germ cell production. The increased growth rate of the fish results in more efficient production from the commercial aquaculture operation [Manzoor Ali P K M, Satyanarayana Rao G P. Growth improvement in carp, *Cyprinus carpio* (Linnaeus), sterilized with 17α-methyltestosterone. Aquaculture 1989; 76: 157-167.]. In addition to exhibiting an increased growth rate, the sterile farmed fish will not be able to reproduce with wild fish if they escape aquaculture containment thereby preventing genetic contamination of the wild fish population.

Grass carp is a common species that is stocked in private ponds and lakes in Indiana and other Midwestern states for aquatic plant management [Department of Ecology SoW. Aquatic Plant Management. 2010. Hyper text transfer protocol world wide web address ecy.wa.gov/programs/wq/plants/management/aqua024.html]. Since the carp routinely escape the private ponds and invade public waterways, the hatcheries that produce the carp are required to sell only genetically sterile fish that are produced by triploidy. Methods of producing triploid fish are not 100% effective, making it necessary for the hatcheries to conduct time consuming and labor intensive genetic testing of each fish before it is sold [Rottmann R W, et al. "Induction and Verification of Triploidy in Fish." In: Southern Regional Aquaculture Center; 1991.].

Additionally, genetically modified fish have found a niche market in aquariums and as privately owned pets. One example is the GloFish®, a genetically modified fluorescing fish, originally bred in a search to develop fish useful in the detection of environmental pollutants. The fish are patented (U.S. Pat. No. 7,834,239) and are intended for aquarium use. It is thought that escape of GloFish® into a local waterway would not pose a detrimental environmental effect, as GloFish® are thought to be unable to survive in a non-tropical environment. However, concern remains over the potential implications of escaped GloFish® and other genetically modified fish intended for aquaculture or aquarium use. Additionally, there are concerns regarding unauthorized breeding and sale of patented or otherwise protected genetically modified fish.

There therefore remains a need in the art to generate large numbers of reproductively sterile fish using methods that can be applied to aquaculture operations and fish for aquarium displays. In addition to aquaculture, the methods developed from this research could also be applied to the prevention and control of invasive fish species and the prevention and control of unauthorized fish breeding.

SUMMARY OF THE INVENTION

The present invention relates to methods of producing large populations of sterile fish, where the sterilization methods include disruption of germ cell development in the fish embryo without affecting any other characteristics resulting in the production of completely normal reproductively sterile fish. The invention also relates to transgenic fish so produced and to methods of preventing genetic contamination of a wild fish population by farmed fish.

In one aspect, the invention relates to a method of producing a reproductively sterile fish, the method including disrupting the Sdf-1a gradient or a Lif signal pathway in a fish embryo to a sufficient extent to prevent primordial germ cell (PGC) migration to and colonization in the gonad of the embryo.

In another aspect, the invention relates to a method of producing a reproductively sterile fish, the method including disrupting a Sdf-1a or a Lif signaling pathway in a fish embryo to a sufficient extent that migration of primordial germ cells (PGCs) to the gonad of the embryo is prevented.

In a further aspect, the invention relates to a method of preventing genetic contamination of a wild fish population by a transgenic fish, the method including introduction to the wild fish population of a transgenic fish comprising a genome transformed with a plasmid construct comprising both a gene encoding Sdf-1a or Lif and a gene directing expression of Sdf-1a or Lif, whereby the transgenic fish is sterile and reproductively incompetent with wild fish of the wild fish population.

A further aspect of the invention relates to a method of monitoring primordial germ cell (PGC) migration in a fish embryo, including the steps of: a) administering a plasmid construct comprising both a gene encoding Sdf-1a or Lif and a gene directing expression of Sdf-1a or Lif, operatively linked to target expression of the Sdf-1a or Lif to primordial germ cells of the fish embryo; b) administering a plasmid construct comprising both a gene encoding a fluorescent protein and a gene directing expression of the fluorescent protein, operatively linked to target expression of the fluorescent protein to the primordial germ cells of the fish embryo; and c) determining location of the fluorescently labeled primordial germ cells within the fish embryo.

A still further aspect of the invention relates to a transgenic fish derived from an embryo including a transgene that is selectively expressed by primordial germ cells (PGCs) of the fish to an extent sufficient to prevent migration of primordial germ cells to the gonad of the embryo.

An additional aspect of the invention relates to a plasmid construct for generation of a transgenic fish of the invention.

Another aspect of the invention relates to a method for preventing breeding of a fish, where the fish is derived from an embryo comprising a transgene that is selectively expressed by primordial germ cells (PGCs) of the fish to an extent sufficient to prevent migration of the primordial germ cells to the gonad of the embryo. The resultant fish is sterile and breeding of the fish cannot be performed.

A further aspect of the invention relates to a method of producing a reproductively controllable fish, including transforming a fish embryo or brood stock fish with a plasmid construct comprising a gene encoding exogenous Sdf-1a or Lif and a 3'UTR fragment of a germ cell specific gene, wherein expression of the exogenous Sdf-1a or Lif in primordial germ cells (PGCs) produces a reproductively sterile fish and suppression of the exogenous Sdf-1a or Lif expression in PGCs produces a reproductively fertile fish.

An additional aspect of the invention relates to a method of producing a double transgenic, reproductively controllable fish, including breeding a first fish transformed with a plasmid construct comprising a pTRE-Tight promoter, a gene encoding Sdf-1a or Lif and a 3' UTR fragment of a germ cell specific gene with a second fish transformed with a plasmid construct comprising a gene encoding Tet-off adv or Tet-on 3G, a promoter and a 3'UTR fragment of a germ cell specific gene to produce a third, reproductively controllable fish.

Other aspects, features and embodiments of the invention will be more fully apparent from the ensuing disclosure and appended claims.

BRIEF DESCRIPTION OF THE DRAWINGS

FIG. 1 provides illustrations of PGC migration during fish embryo development, under various conditions.

DETAILED DESCRIPTION OF THE INVENTION, AND PREFERRED EMBODIMENTS THEREOF

The present invention relates to sterilization of fish. The methods of the invention are highly efficient, cost-effective methods to generate sterile fish, effective both on a small scale and on a large scale. The sterilization strategy will specifically disrupt germ cell development in a fish embryo without affecting any other characteristics, resulting in the production of completely normal reproductively sterile fish. The invention also provides fish generated according to methods of the invention.

Two methods are commonly used to induce sterility in fish. The first method is the manipulation of the chromosome number by triploidization or interspecies hybridization and the second method is the disruption of the gonadotropin-releasing hormone (GnRH) pathway using antisense RNA or treatment with gamma aminobutyric acid (GABA). Each of these methods has disadvantages.

Chromosome set manipulation is used to produce triploid fish. Triploid fish contain three sets of chromosomes, rather than two. Triploid fish generally cannot reproduce, however chromosome set manipulation does not always result in sterility of 100% of the treated fish. For example, studies done on triploid rainbow trout [Arai K., "Genetic improvement of aquaculture finfish species by chromosome manipulation techniques in Japan." *Aquaculture* 2001; 197: 205-228.] and Atlantic salmon [Donaldson E M, et al., "Current status of induced sex manipulation." In: Proceedings of the Third International Symposium on Reproductive Physiology of Fish 1987. 108-119.] found that male fish were seldom completely sterile and many of the treated Atlantic salmon females continued to possess a small number of oocytes that could be fertilized [Johnstone R., "Maturity control in Atlantic salmon." In: Muir J F, Roberts R J (eds.), Recent advances in aquaculture. London: Blackwell Scientific Publications; 1993: 69-77.]. It is desirable to develop methods of sterilization that are more consistent and which demonstrate high efficacy of sterilization, preferably approaching 100%.

Another disadvantage of chromosome set manipulation is that it requires that specific methods be developed for each species of fish being treated [Arai K., "Genetic improvement of aquaculture finfish species by chromosome manipulation techniques in Japan." *Aquaculture* 2001; 197: 205-228.]. As such, no one method is applicable across multiple species of fish.

Gonadotropin-releasing hormone (GnRH) is a pituitary hormone that is required to maintain a normal reproductive cycle in vertebrates. Specifically, GnRH stimulates the synthesis and secretion of the gonadotropins: follicle-stimulating hormone (FSH) and luteinizing hormone (LH). Generally, the gonads are the primary target organs for LH and FSH. LH and FSH are integral to the reproductive system and inhibition of GnRH signaling and, therefore, disruption of the synthesis and secretion of LH and FSH is a potent method to induce infertility.

Disruption of the GnRH pathway has been accomplished in several species of fish by the introduction of a transgene that encodes antisense RNA that blocks endogenous GnRH expression [Uzbekova S, et al., "Transgenic rainbow trout expressed sGnRH-antisense RNA under the control of sGnRH promoter of Atlantic salmon." *J. Mol. Endocrinol.* 2000; 25: 337-350; Hu W, et al. "Antisense for gonadotropin-releasing hormone reduces gonadotropin synthesis and gonadal development in transgenic common carp (*Cyprinus carpio*)." *Aquaculture* 2007; 271: 498-506.]. Some studies have shown however that low levels of GnRH expression persist in the transgenic fish resulting in a failure to completely induce sterility [Uzbekova S, et al., "Transgenic rainbow trout expressed sGnRH-antisense RNA under the control of sGnRH promoter of Atlantic salmon." *J. Mol. Endocrinol.* 2000; 25: 337-350.].

Another disadvantage of this strategy is that it is difficult to maintain a fertile population of fish for brood stock. Since the gene encoding the antisense RNA is integrated into the genome and continuously expressed, all of the fish will carry it, making it necessary to administer exogenous GnRH to individual fish by injection to maintain a fertile brood stock population.

Additionally, GnRH injection of brood stock is not practical in a large-scale commercial aquaculture operation.

Treatment with γ-aminobutyric acid (GABA) has also been proposed to disrupt the GnRH signaling pathway in fish [U.S. Pat. No. 7,194,978.]. Since GABA regulates GnRH neuron development in the embryo, treatment with exogenous GABA is able to disrupt the formation and normal migration pattern of the GnRH neurons [Fueshko S M, et al., "GABA inhibits migration of luteinizing hormone-releasing hormone neurons in embryonic olfactory explants." *J Neurosci* 1998; 18: 2560-2569.]. Although this approach has been used successfully in the laboratory, it is not practical on a commercial scale due to the expense and labor required to treat large populations of fish. Also, the treatment affects other physiological and neurological functions in addition to gonad development in the fish.

The present invention provides a method of producing sterilized fish which is useful, efficient and cost-effective for sterile fish production. The methods are generally applicable to both small scale and large scale fish sterilization. The method relates to disruption of germ cell development in the fish to be sterilized.

Figure 1A:
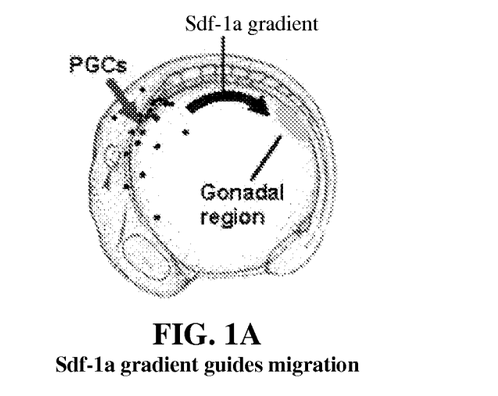
FIG. 1A illustrates the normal migration of PGCs (solid arrow) along a gradient of Sdf-1a (curved arrow) to the gonadal region (shaded oval)
Figure 1B:
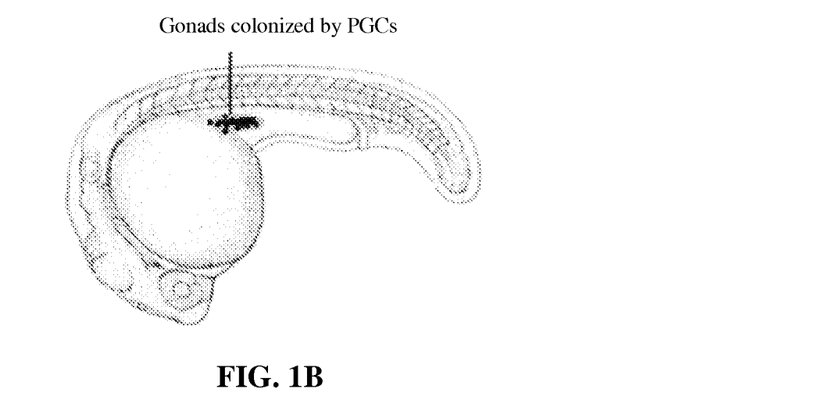
FIG. 1B illustrates PGCs colonized in the gonads (shaded oval), upon completion of migration along a Sdf-1a gradient.

Primordial germ cells (PGCs) are a population of cells in the fish embryo that are precursors to the gametes of the adult fish. The PGCs are produced during the very early stages of embryo development before individual tissues and organs begin to form. At later stages of normal embryo development, as the individual organs are forming, the PGCs migrate through the embryo from their original location to the area of the gonadal precursors (FIG. 1A, B). At the end of their migration the PGCs enter the developing gonads and colonize the tissue.

When the embryo eventually undergoes sexual differentiation, the gonad completes development to form a testis or ovary in the male or female, respectively, and the PGCs that previously colonized the gonad differentiate to produce either sperm or eggs, respectively. This same basic scenario of gonad formation and germ cell migration and differentiation is found in all vertebrates including fish and mammals [Doitsidou M, et al., "Guidance of primordial germ cell migration by the chemokine SDF-1." *Cell* 2002; 111: 647-659; Molyneaux K A, et al., "The chemokine SDF1/CXCL12 and its receptor CXCR4 regulate mouse germ cell migration and survival." *Development* 2003; 130: 4279-4286.].

Several laboratories that have studied PGC migration have shown that the general molecular mechanism is conserved among vertebrate species. For example, in species as diverse as fish and mice, the molecular cue that guides the migrating PGCs to the gonadal tissue is a protein called stromal cell-derived factor-1a (Sdf-1a). The PGCs possess the Sdf-1a receptor on their surface which allows the cells to recognize the protein and migrate along a concentration gradient towards the gonadal region, the source of the Sdf-1a. The Sdf-1a gradient provides the directional cue that guides the PGCs to the gonadal region. The mechanism of PGC migration is highly conserved among various species of fish. The PGCs may be active or passive in migration toward the gonadal region.

Disruption of the Sdf-1a gradient correspondingly disrupts the PGC migration to the gonadal region.

Figure 2:
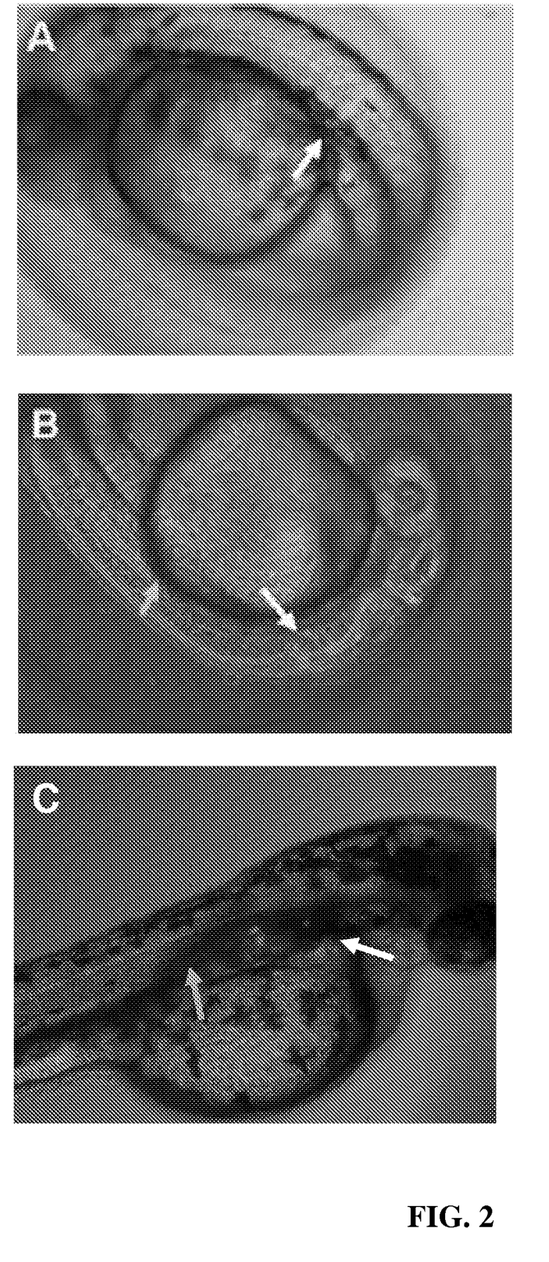
FIG. 2 is a fluorescence photomicrograph showing (A) a normal control embryo with gonad colonized by fluorescently labeled PGCs (white arrow), (B) an embryo in which the PGCs (white arrow) were induced to produce their own Sdf-1a which prevented the cells from migrating to the gonad (shaded arrow) and (C) an embryo in which the PGCs (white arrow) were induced to produce their own Lif which also prevented the cells from migrating to the gonad (shaded arrow).

As illustrated in FIG. 2C, the present inventors have demonstrated that over expression of leukemia inhibitory factor (Lif), in PGCs also disrupts the guidance of migrating PGCs to the gonadal tissue. Lif is a protein cytokine belonging to the interleukin 6 class that affects cell growth and development.

In one embodiment, the invention provides a method to efficiently disrupt PGC migration in large numbers of fish embryos, resulting in large-scale production of reproductively sterile adult fish. The invention contemplates various suitable methods of disruption of such migration. The methods of the invention are also applicable to single embryos in smaller scale production of reproductively sterile adult fish.

It has been previously shown that ablation of PGCs results in the development of a sterile adult fish that is devoid of gametes [Slanchev K, et al., "Development without germ cells: the role of the germ line in zebrafish sex differentiation." *Proc Natl Acad Sci* USA 2005; 102: 4074-4079.].

In normal development, PGCs migrate along the Sdf-1a gradient toward the gonadal region (FIG. 1A; FIG. 1B; FIG. 2A). The methods of the invention comprise disruption of this normal migration by forcing the PGCs to produce their own Sdf-1a or Lif. This can be achieved by administration of plasmids containing an Sdf-1a or Lif gene to an embryo, where the Sdf-1a or Lif gene is operatively linked to a gene that will direct the Sdf-1a or Lif gene to expression in the PGCs.

Expression of Sdf-1a by the PGCs in the fish embryo is performed in an amount sufficient to saturate the Sdf-1a receptors, thereby preventing the PGCs from recognizing the normal gradient that would guide them to the developing gonad. Sdf-1a receptors are known to be present both on the surface of the PGCs and within the somatic environment. As a result of expression of Sdf-1a by the PGCs, the PGCs migrate to ectopic locations and are prevented from colonizing the gonad.

Expression of Lif by the PGCs in the fish embryo is performed in an amount sufficient to disrupt a Lif signaling pathway, thereby preventing the PGCs from recognizing the normal gradient that would guide them to the developing gonad. These strategies have the advantage of efficiently inducing sterility in 100% of the treated individuals without affecting any other physiological characteristics of the fish.

Figure 1C:
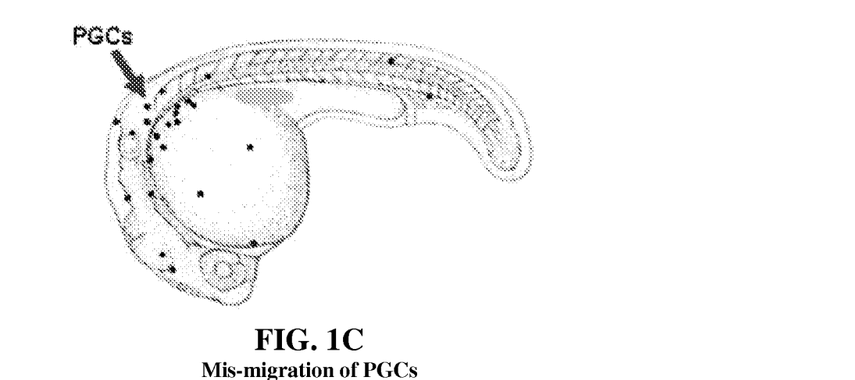
FIG. 1C illustrates the results of PGC (solid arrow) migration when the Sdf-1a gradient is disrupted.

As demonstrated by the examples set forth herein, the present inventors have shown that disruption of the Sdf-1a signaling pathway or of a Lif signaling pathway leads to the failure of the PGCs to migrate properly (FIG. 1C; FIG. 2B; FIG. 2C). In FIG. 1C it is seen that the PGCs fail to reach the area of the gonadal precursors upon disruption of the Sdf-1a signaling pathway. FIG. 2B is a photograph of the results of the experiment set forth in Example 2, illustrating that induction of PGC production of Sdf-1a resulted in failure of the PGCs to reach the area of the gonadal precursors. FIG. 2C is a photograph of the results of the experiment illustrating that induction of PGC production of Lif resulted in failure of the PGCs to reach the area of the gonadal precursors.

In one embodiment, the invention provides a method of producing a reproductively sterile fish, the method including disrupting an Sdf-1a signaling pathway in a fish embryo to a sufficient extent that migration of primordial germ cells (PGCs) to the gonad of the embryo is prevented.

In another embodiment the invention provides a method of producing a reproductively sterile fish, the method including inducing expression of Sdf-1a in a fish embryo in an amount effective to disrupt the Sdf-1a gradient in the embryo to a sufficient extent to prevent primordial germ cell (PGC) migration to and colonization in the gonad of the embryo.

In another embodiment, the invention provides a method of producing a reproductively sterile fish, the method including disrupting a Lif signaling pathway in a fish embryo to a sufficient extent that migration of primordial germ cells (PGCs) to the gonad of the embryo is prevented.

In another embodiment the invention provides a method of producing a reproductively sterile fish, the method including inducing expression of Lif in a fish embryo in an amount effective to disrupt the primordial germ cell (PGC) migration to and colonization in the gonad of the embryo.

Zebrafish were selected for initial exemplification of the methods of the invention, due to their short generation time and large numbers of embryos produced per mating, which are easily obtained on a daily or weekly basis. Additionally, the embryos of zebrafish are transparent, providing ease of visual observations, and are hardy. The normal migration of PGCs within the embryo is an evolutionarily conserved mechanism and is found in all fish. Accordingly, the methods of the invention are applicable to all fish species, including, but not limited to, zebrafish, carp, trout and salmon.

As described herein, the methods are generally applicable to farmed fish, as production of sterile farmed species is desirable. Accordingly, the methods of the invention are applicable to any farmed species of fish, particularly to commercially important species.

By the methods of the present invention, transgenic fish are generated, which express Sdf-1a or Lif specifically in the PGCs during the short window of time that coincides with PGC migration.

The invention, in one embodiment, relates to a transgenic fish or a population of transgenic fish, derived from an embryo comprising a transgene that is selectively expressed by primordial germ cells of the fish, to an extent sufficient to prevent migration of primordial germ cells to the gonad of the embryo.

"Transgenic" as used herein refers to the intentional introduction of a foreign gene or genetic construct into the genome of a target animal. By the methods of the present invention, transgenic fish are generated. As described herein, particular transgenic fish are generated by the introduction of an Sdf-1a or Lif gene into the genome of a fish and subsequent expression of the gene. Introduction of such gene to the genome of the fish may be performed by any method known for introduction of nucleic acid into animals to produce a transgenic animal, including fish. Such methods of introduction may include, but are not limited to, pronuclear microinjection; gene transfection into embryonic stem cells; gene targeting into embryonic stem cells; and electroporation of embryos.

Transgenic fish generated by the methods of the invention are therefore sterile. Use of such transgenic fish in aquaculture systems or in aquariums eliminates concerns relating to invasion of such fish into a natural environment. If the fish in aquaculture or in an aquarium were to escape into a local waterway or other water system, the sterility of the fish would prevent the escaped fish from genetically contaminating any wild fish population in the environment. Furthermore, sterile transgenic fish generated by the methods of the invention may be intentionally released into an environment, where the fish cannot breed with any wild fish population in the environment.

Additionally, the sterile transgenic fish are useful to prevent unauthorized fish breeding of patented or otherwise protected genetically modified fish, where the sterile genetically modified fish cannot be bred.

The invention, in a further embodiment, provides a method of preventing genetic contamination of a wild fish population by a transgenic fish, the method including introduction to the wild fish population of a transgenic fish comprising a genome transformed with a plasmid construct comprising both a gene encoding Sdf-1a or Lif and a gene directing expression of Sdf-1a or Lif, whereby the transgenic fish is sterile and reproductively incompetent with wild fish of the wild fish population.

As described herein, the methods of the invention include targeted expression of Sdf-1a or Lif by the PGCs. In practice of the invention, any method can be used to drive expression of the encoded amino acid sequence from a nucleic acid by the PGC. Such methods include, but are not limited to, constructing a nucleic acid with expression driven by a regulatory element. Such regulatory elements may be DNA sequences that regulate the expression of other DNA sequences at the level of transcription and may include, but are not limited to, promoters, enhancers, and the like. In various embodiments of the invention the promoter may be, but is not limited to: a vasa promoter, a kop promoter, a nanos promoter, a pTRE3G promoter a pTRE-Tight promoter, a heat-shock protein (hsp) promoter and a metallothionein II (mt-II) promoter.

Further in practice of the invention, the Sdf-1a or Lif is targeted to the PGCs. Any method for directed expression or transport of the expressed Sdf-1a or Lif can be used. nanos is a germ cell specific gene whose three prime untranslated region (3'UTR) carries a specific signal to direct and limit the expression of nanos in PGCs. In one embodiment, the methods of the invention include such a signal sequence with a gene encoding Sdf-1a or Lif. Additionally, any other signal sequences, or transport sequence may be used to direct expression or transport of the expressed Sdf-1a or Lif. Such sequences may include, but are not limited to, 3'UTR regions of other genes such as vasa 3'UTR and deadend (dnd) 3'UTR.

In a further embodiment the targeted expression of Sdf-1a or Lif by the PGCs comprises use of an inducible expression system. As used herein "inducible expression system" refers to controlled gene expression that has flexibility with regard to timing, direction, duration and location of expression of the gene. The combination of the particular inducible expression system and the promoter used in that system results in the targeted expression of Sdf-1a or Lif by the PGCs.

In a particular embodiment the inducible expression system includes co-expression of both a target gene and nanos 3'UTR. nanos is a germ cell specific gene whose 3'UTR carries a specific signal to direct and limit the expression of nanos in PGCs. By combining the 3' UTR from nanos with the gene encoding Sdf-1a or Lif, the system leads to prolonged and specific expression of Sdf-1a or Lif in PGCs of the fish embryo.

In a further embodiment a fluorescent indicator is transgenically expressed within the fish embryo for use in determining the location of a PGC within the embryo. The PGCs were identified by fluorescence of the indicator. Detection of the fluorescent indicator may be performed by any known method.

In an exemplary embodiment the fluorescent indicator is a green fluorescent protein (GFP). GFP emits bright green light when simply exposed to UV or blue light, unlike other bioluminescent reporters. Fluorescence of GFP is species-independent and requires no substrate, cofactor, or additional proteins for illuminating green light. The fluorescent indicator may also be a mutant of GFP, such as, but not limited to alter GFPs with varied codon structure and corresponding altered green fluorescent intensity, blue fluorescent protein (EBFP), cyan fluorescent protein (ECFP), yellow fluorescent protein (YFP). In an additional embodiment the fluorescent indicator is a red fluorescent protein (RFP)

The present invention contemplates use of any known fluorescence protein which can be transgenically expressed in a fish embryo and used to indicate the location of the PGCs in the embryo.

The invention, therefore, in a particular embodiment, relates to a method of monitoring primordial germ cell migration in a fish embryo where the method includes administering a plasmid construct including a gene encoding a fluorescent protein targeted for specific expression in the PGCs of the embryo.

In a still further embodiment, the invention provides methods of producing reproductively controllable fish. In one embodiment the method includes transforming a fish embryo or brood stock fish with a plasmid construct comprising a gene encoding exogenous Sdf-1a or Lif and a 3'UTR fragment of a germ cell specific gene, wherein expression of the exogenous Sdf-1a or Lif in PGCs produces a reproductively sterile fish and suppression of the exogenous Sdf-1a or Lif expression in the PGCs produces a reproductively fertile fish.

In a further embodiment, the reproductively controllable fish is a double transgenic, reproductively controllable fish, produced by breeding a first fish transformed with a plasmid construct comprising a gene encoding Sdf-1a or Lif and a 3'UTR fragment of a germ cell specific gene with a second fish transformed with a plasmid construct comprising a gene encoding Tet-off adv or Tet-on 3G, a promoter and a 3'UTR fragment of a germ cell specific gene to produce a third, reproductively controllable fish. Control of the Sdf-1a or Lif expression in PGCs by induction or suppression controls the reproductive abilities of the fish.

The invention therefore provides methods, fish and plasmid constructs relating to the efficient sterilization of fish by disruption of the Sdf-1a signaling pathway or a Lif signaling pathway, leading to the failure of normal PGC migration in the embryo of the fish. Using the methods of the invention, large-scale and small-scale production of sterilized fish may be achieved, quickly, reproducibly, and simultaneously in multiple fish of a population. Consequently, the methods disclosed herein prevent the genetic contamination of wild type fish by transgenic fish or the unauthorized breeding of transgenic fish, as the transgenic fish are sterile.

The advantages and features of the invention are further illustrated with reference to the following examples, which are not to be construed in any way as limiting the scope of the invention but rather as illustrative of various embodiments of the invention in specific applications thereof.

Example 1

Targeted Expression of DsRED in PGCs

The present inventors have performed targeted expression of *Discosoma* sp. red fluorescent protein (DsRED) in PGCs of zebrafish embryos. In multiple experiments, the DsRED was expressed in PGCs under the control of various promoters: a vasa promoter, a kop promoter, and a nanos promoter. All transfections resulted in specific red fluorescence of PGCs.

Example 2

Targeted Expression of DsRED and SDF-1a in PGCs

Plasmid constructs sdf-1a-nanos-3'UTR and DsRed-nanos-3'UTR were constructed in vitro.

DsRed-nanos-3'UTR was injected into a one-cell stage embryo and PGC position was detected by measuring fluorescence. Results are demonstrated in FIG. 2A, where the normal migration of PGCs was observed.

The plasmid constructs of sdf-1a-nanos-3'UTR and DsRed-nanos-3'UTR were combined to form an RNA mix that was injected into one-cell stage embryos. Results are demonstrated in FIG. 2B, where the nanos-3'UTR was observed to direct expression to the PGCs with particularity and the overexpression of Sdf-1a by the PGCs was observed to prevent the PGCs from following a normal migration pattern.

Example 3

Targeted Expression of DsRED and Lif in PGCs

Plasmid constructs lif-nanos-3'UTR and DsRed-nanos-3'UTR were constructed in vitro.

DsRed-nanos-3'UTR was injected into a one-cell stage embryo and PGC position was detected by measuring fluorescence. Results are demonstrated in FIG. 2A, where the normal migration of PGCs was observed.

The plasmid constructs of lif-nanos-3'UTR and DsRed-nanos-3'UTR were combined to form an RNA mix that was injected into one-cell stage embryos. Results are demonstrated in FIG. 2C, where the nanos-3'UTR was observed to direct expression to the PGCs with particularity and the overexpression of Lif by the PGCs was observed to prevent the PGCs from following a normal migration pattern.

Example 4

Inducible Promoter Systems for Targeted Expression of SDF-1a or Lif in PGCs

The invention provides methods of using an inducible gene expression system to generate transgenic zebrafish that express Sdf-1a or Lif specifically in the PGC population of the embryo only during the short window of time when the PGCs are actively migrating.

Figure 3:
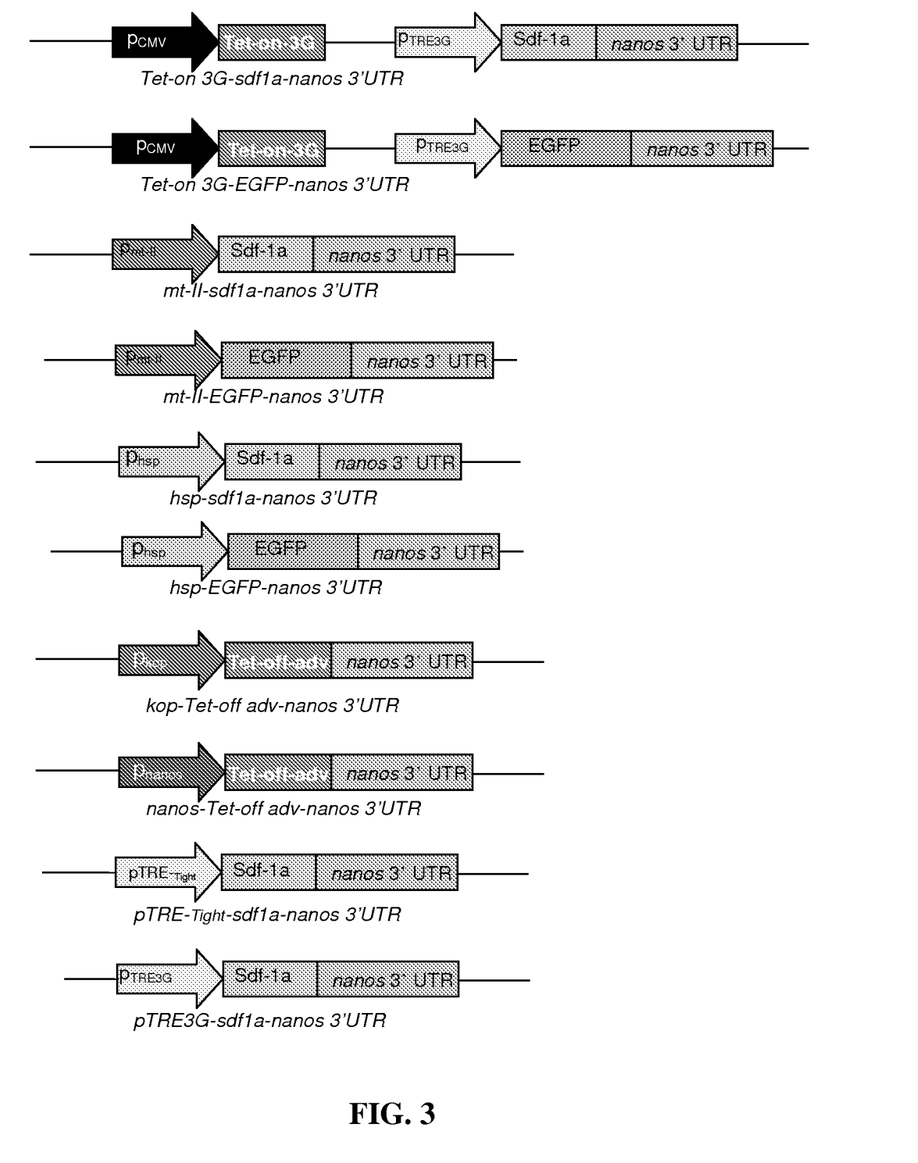
FIG. 3 is a diagram of the plasmid constructs useful to generate transgenic fish of the invention.

To accomplish this targeted expression, four inducible promoter systems have been designed and combined with a specific targeting strategy to express Sdf-1a or Lif only in PGCs. The expression system makes use of the 3' untranslated region (3'UTR) from the nanos gene and germ cell specific promoters, kop and nanos. To control the timing of Sdf-1a or Lif expression to coincide with PGC migration, the inducible expression system will employ an inducible promoter such as the pTRE3G, metallothionein II (mt-II), heat-shock protein (hsp) or pTRE-Tight promoters, which are induced by treating the embryos (FIG. 4) or stock fish (FIG. 5) with either doxycycline, zinc chloride, heat shock or no treatment, respectively. Another induction procedure can be achieved in a Tet-off system, by crossing two different transgenic brood stocks (FIG. 6) to generate sterile fish. To visualize the PGCs, a green fluorescent protein, (EGFP) gene under the control of the promoter will also be included (FIG. 3).

Transgenic lines of zebrafish that carry each of the following transgene constructs: mt-II-sdf1a-nanos 3'UTR and mt-II-EGFP-nanos 3'UTR, pTRE-Tight-sdf1a-nanos 3'UTR, Tet-on 3G-lif-nanos 3'UTR mt-II-lif-nanos 3'UTR and hsp-lif-nanos 3'UTR, kop-Tet-off adv-nanos 3'UTR, nanos-Tet-off adv-nanos 3'UTR, kop-Tet-on 3G-nanos 3'UTR or nanos-Tet-on 3G-nanos 3'UTR will be generated. Transgenic lines of zebrafish that carry each of the following transgene constructs: pTRE3G-sdf1a-nanos 3'UTR and pTRE3G-EGFP-nanos 3'UTR, hsp-sdf1a-nanos 3'UTR and hsp-EGFP-nanos 3'UTR have been generated and examined, as detailed below.

Figure 4:
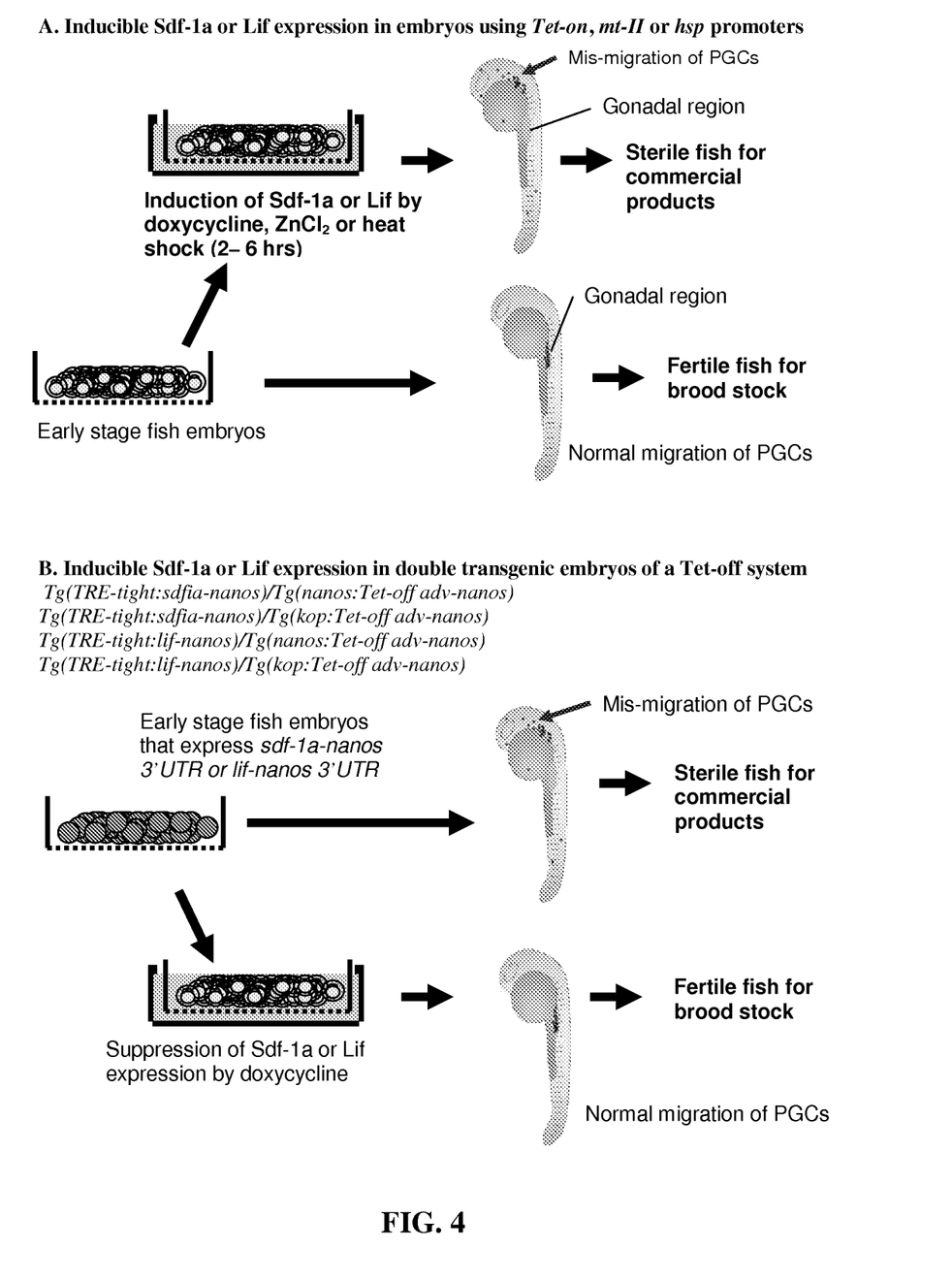
FIG. 4 is a flow chart, illustrating the methods of producing sterile fish and fertile brood stock by treating embryos in an inducible system.

The transgenic embryos will be incubated with the appropriate inducer (either doxycycline, zinc chloride or heat shock) at various time intervals and concentrations or no treatment for double transgenic embryos from Tet-off system to optimize the transgene induction protocol and PGC migration will be monitored by fluorescence microscopy (FIG. 4). The fish will be raised to sexual maturity to confirm sterility and gonadal development characterized by histological examination. Also, the fertility of several large groups of non-induced fish will be examined to determine if background (non-induced) expression of the transgene is occurring.

Figure 5:
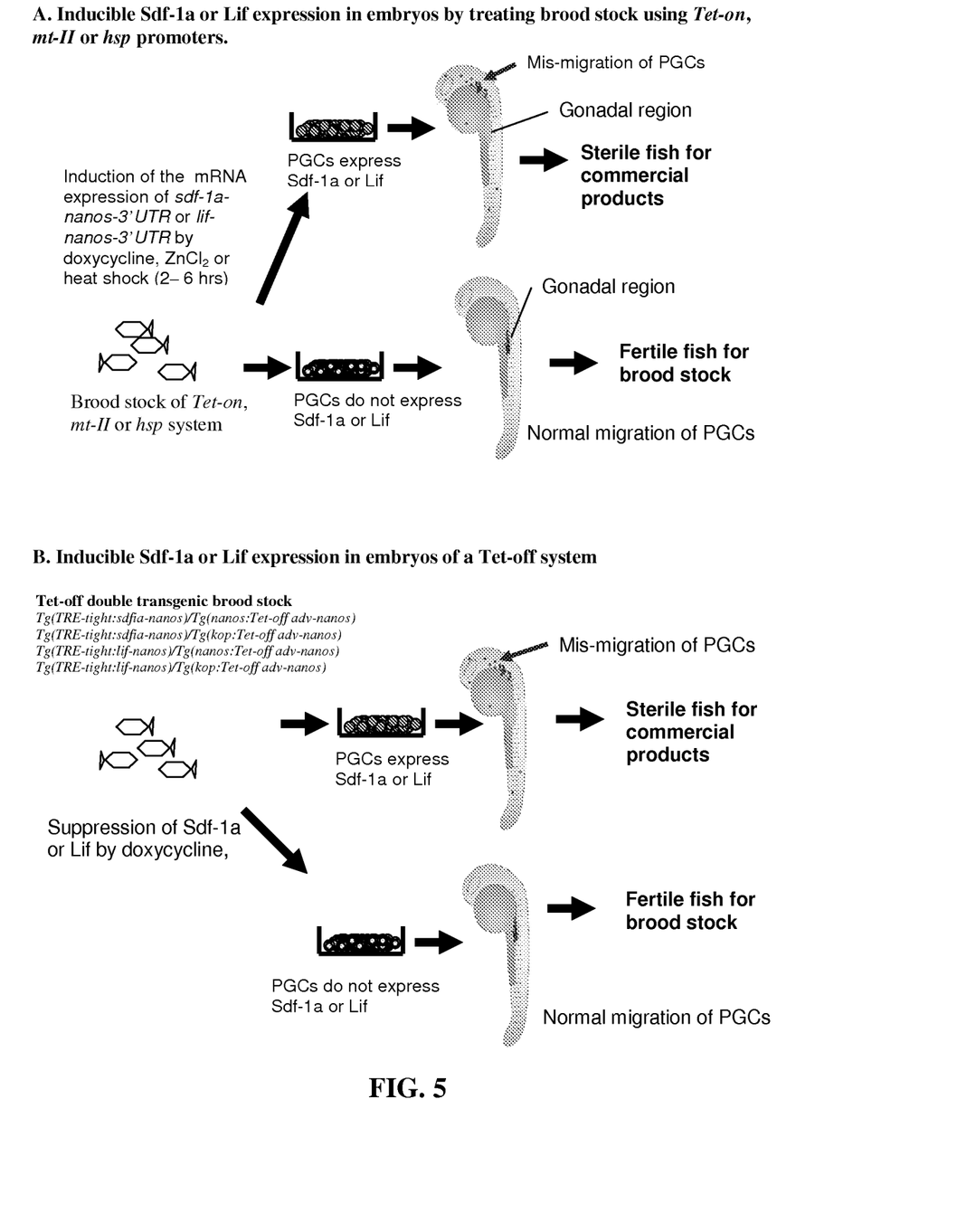
FIG. 5 is a flow chart, illustrating the methods of producing sterile fish and fertile brood stock by treating adult fish in an inducible system.
Figure 6:
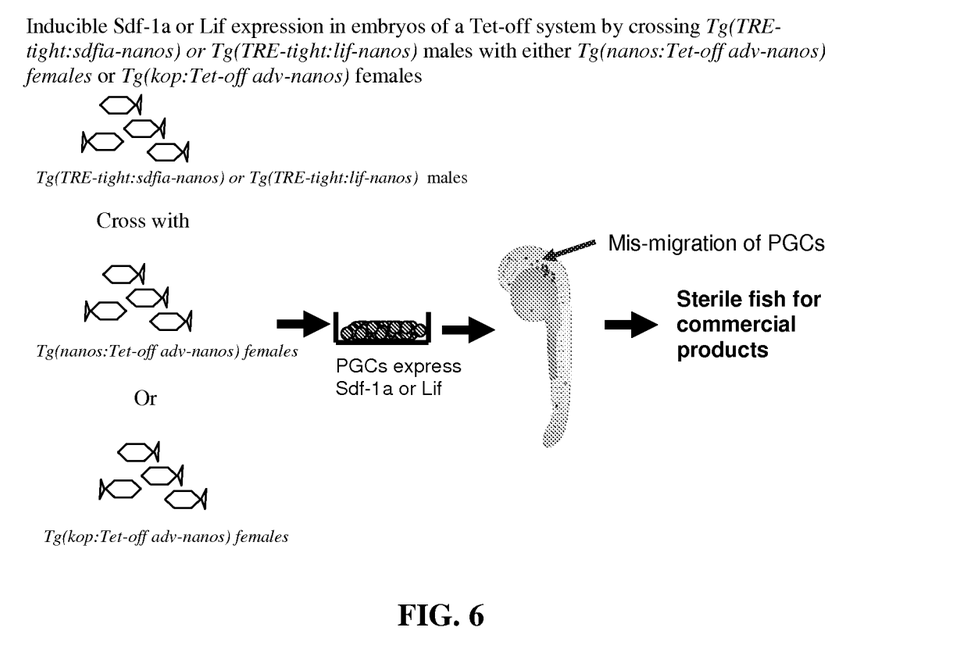
FIG. 6 is a flow chart, illustrating the methods of producing sterile fish by crossing Tg(TRE-tight:sdfia-nanos) or Tg(TRE-tight:lif-nanos) males with either Tg(nanos:Tet-off adv-nanos) females or Tg(kop: Tet-off adv-nanos) females.

Except in the Tet-off system, the transgenic adult stock will be incubated with the appropriate inducer (either doxycycline, zinc chloride or heat shock) at various time intervals and concentrations to optimize the transgene induction protocol and PGC migration will be monitored by fluorescence microscopy (FIG. 5). The fish will be raised to sexual maturity to confirm sterility and gonadal development characterized by histological examination. Also, the fertility of several large groups of non-induced fish will be examined to determine if background (non-induced) expression of the transgene is occurring.

Figure 7:
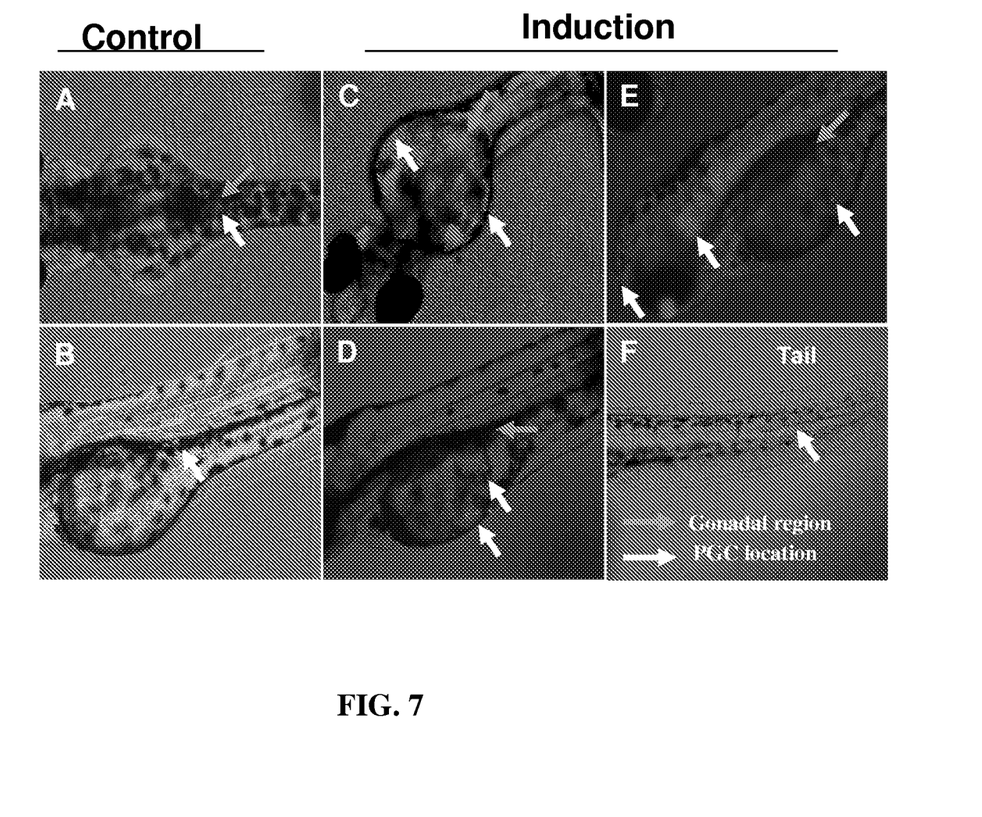
FIG. 7 is a fluorescence photomicrograph showing (A, B) a normal control embryo with gonadal region (shaded arrow) colonized by fluorescently labeled PGCs (white arrow), (C-F) an embryo in which the PGCs (white arrow) were induced to produce their own Sdf-1a which prevented the cells from migrating to the gonad (shaded arrow).

Incubation of embryos transformed with hsp-sdf1a-nanos 3'UTR and hsp-EGFP-nanos 3'UTR with heat shock at 34.5° C. for 6 hours (C, D) or with pTRE3G-sdf1a-nanos 3'UTR and pTRE3G-EGFP-nanos 3'UTR with doxycycline at 1000 ng/ml for 2.3 hours (E, F) was performed as set forth above and the results are set forth in FIG. 7. FIG. 7 is a fluorescence photomicrograph showing (A, B) a normal control embryo with gonadal region (shaded arrow) colonized by fluorescently labeled PGCs (white arrow), and (C-F) an embryo in which the PGCs (white arrow) were induced to produce their own Sdf-1a which prevented the cells from migrating to the gonad (shaded arrow).

The adult stock of double transgenic Tet-off system will be produced by incubating embryos transformed with kop-Tet-off adv-nanos 3'UTR and pTRE-Tight-sdf1a-nanos 3'UTR or nanos-Tet-off adv-nanos 3'UTR and pTRE-Tight-sdf1a-nanos 3'UTR with doxycycline at various time intervals and concentrations to optimize the transgene suppression protocol and PGC migration will be monitored by fluorescence microscopy (FIG. 4B). The fish will be raised to sexual maturity to confirm fertility and gonadal development characterized by histological examination.

Figure 8:
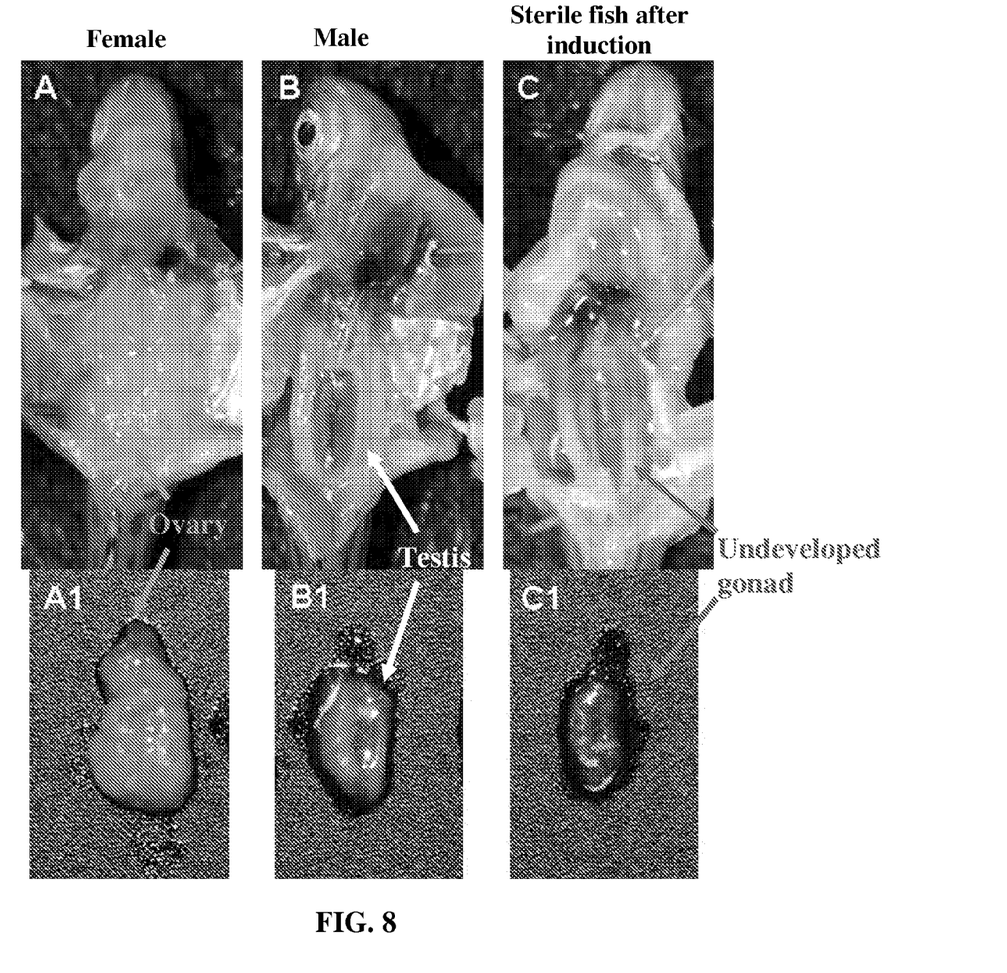
FIG. 8 is a photomicrograph showing (A, A1) a normal control embryo developed into a fertile female, with full developed ovary, (B, B1) a normal control embryo developed into a fertile male, with full developed testis and (C, C1) an embryo in which the PGCs were induced to produce their own Sdf-1a which prevented the cells from migrating to the gonad resulting in sterile fish with undeveloped gonad.

FIG. 8 is a photomicrograph showing (A, A1) a normal control embryo developed into a fertile female, with full developed ovary, (B, B1) a normal control embryo developed into a fertile male, with full developed testis and (C, C1) an embryo in which the PGCs were induced to produce their own Sdf-1a which prevented the cells from migrating to the gonad resulting in sterile fish with undeveloped gonad.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A method of producing a reproductively sterile fish, the method comprising:
   (a) disrupting an Sdf-1a gradient in a fish embryo to a sufficient extent to prevent primordial germ cell (PGC) migration to and colonization in the gonad of the embryo to produce a reproductively sterile fish, wherein the disrupting of an Sdf-1a gradient comprises inducing expression of Sdf-1a by the PGCs by use of an inducible gene expression system comprising a heat shock promoter operably linked to the Sdf-1a gene, and
   (b) growing said embryo to an adult fish,
   wherein said adult fish is devoid of gametes.

2. The method of claim 1, wherein the inducible gene expression system comprises a plasmid construct comprising a gene encoding Sdf-1a and a 3'UTR fragment of a germ cell specific gene.

3. The method of claim 2, wherein the gene encoding Sdf-1a and the 3'UTR fragment of a germ cell specific gene are operatively linked to target expression of the Sdf-1a to primordial germ cells of the fish embryo.

4. The method of claim 3, wherein the germ cell specific gene is selected from the group consisting of nanos and kop.

5. The method of claim 1, wherein the inducing expression of Sdf-1a by the PGCs is conducted in a population of embryos.

6. The method of claim 1, wherein the fish is zebrafish, carp, trout, salmon or other pet and farmed fish.

7. A transgenic fish produced by the method of claim 1.

8. A method of producing an embryo that when grown produces a reproductively sterile fish, the method comprising:
   (a) generating an embryo from a reproductively competent fish; and
   (b) disrupting an Sdf-1a gradient in the fish embryo to a sufficient extent that migration of primordial germ cells (PGCs) to the gonad of the embryo is prevented, wherein the disrupting of an Sdf-1a gradient comprises inducing expression of Sdf-1a by the PGCs by use of an inducible gene expression system comprising a heat shock promoter operably linked to the Sdf-1a gene,
   wherein said embryo in which said Sdf-1a gradient is disrupted will develop into an adult fish that is devoid of gametes.

* * * * *